United States Patent [19]

Engelhardt et al.

[11] Patent Number: 4,585,845
[45] Date of Patent: Apr. 29, 1986

[54] PHOSPHONIC ACID CROSS-LINKED HYDROPHILIC COPOLYMERS

[75] Inventors: Friedrich Engelhardt, Frankfurt am Main; Klaus Kühlein, Kelkheim; Juliane Balzer, Frankfurt am Main; Walter Dürsch, Königstein; Hans-Jerg Kleiner, Kronberg, all of Fed. Rep. of Germany

[73] Assignee: Cassella Aktiengesellschaft, Frankfurt am Main, Fed. Rep. of Germany

[21] Appl. No.: 597,839

[22] Filed: Apr. 9, 1984

[30] Foreign Application Priority Data

Apr. 22, 1983 [DE] Fed. Rep. of Germany ....... 3314569

[51] Int. Cl.$^4$ ........................................... C08F 230/02
[52] U.S. Cl. ........................................ 526/240; 524/2; 8/553; 8/554; 526/258; 526/264; 526/278
[58] Field of Search ................. 526/240, 278, 264, 258

[56] References Cited

U.S. PATENT DOCUMENTS 3,551,394 12/1970 Sakuragi ............................. 526/212
4,368,043 1/1983 Yamauchi ........................... 526/278

FOREIGN PATENT DOCUMENTS 1130177 5/1962 Fed. Rep. of Germany ...... 526/278
1135176 8/1962 Fed. Rep. of Germany ...... 526/278
1077215 7/1967 United Kingdom ................ 526/278

Primary Examiner—Christopher A. Henderson
Attorney, Agent, or Firm—Connolly and Hutz

[57] ABSTRACT

Crosslinked copolymers wherein crosslinking is effected with crosslinking bridge members of the formula

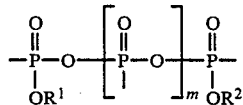

wherein $R^1$ and $R^2$ independently of one another are each hydrogen or alkyl with 1 to 4 carbon atoms and m represents a number from 0 to 6 are prepared by copolymerization of monomers with vinylphosphonic acid (ester)-anhydrides and the new crosslinked polymers according to the invention are suitable for the preparation of acid-soluble coatings and encapsulation materials.

7 Claims, No Drawings

PHOSPHONIC ACID CROSS-LINKED HYDROPHILIC COPOLYMERS

It is know (U.S. Pat. No. 4,085,167, German Auslegeschrift No. 1,135,173) that water-soluble monomers can be copolymerised with olefinically polyunsaturated compounds to give copolymers which are capable, depending on the monomer composition, of absorbing various amounts of water, while swelling, the swelling ability as a rule increasing as the amount of crosslinking agent (polyolefinic component) decreases. Hydrophilic copolymers crosslinked in this manner, especialy those based on acrylic acid methacrylic acid, are used, for example as thickeners, in many ways (printing pastes, cosmetics). Another field of use for such polymers of high swelling ability is the hygiene sector, such polymers being used as a result of their high absorbency.

Crosslinked hydrophilic polymers are also used for consolidation and water retention in soils.

It has now been found that crosslinked hydrophilic copolymers in which crosslinking is effected via bridge members of the formula I

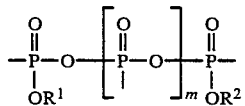

(I)

wherein $R^1$ and $R^2$ independently of one another denote hydrogen or alkyl with 1 to 4 C atoms and m represents a number from 0 to 6, have particular properties which are technologically very useful.

The copolymers according to the invention have the structure of a polymer network in the alkaline, neutral and weakly acid range (ph≧2), this network being split at pH values <2, that is to say by stronger acids. They are therefore directly soluble in stronger aqueous acids, but are only swellable in alkaline to weakly acid aqueous solutions at pH values above 2; they thus offer the possibility of an exactly controllable degradation in the acid pH range.

The new polymers according to the invention are therefore outstandingly suitable, for example, for the preparation of acid-soluble coatings and encapsulating materials.

The possibility of seriously modifying the structure of the copolymers according to the invention by the action of acids is probably attributable to the fact that the crosslinking bridge members of the formula I can be split hydrolytically in the acid pH range according to the following equation

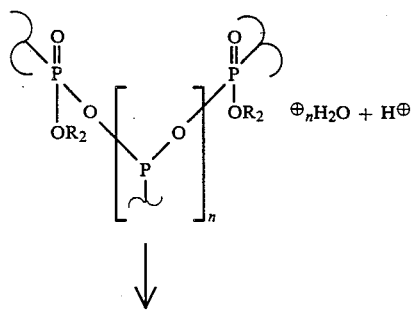

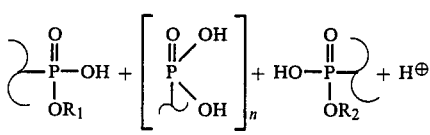

whereupon the swollen polymer loses its gel structure and is transformed into a non-crosslinked soluble polymer structure (in the above equation, the symbol ∼ represents the basic chains of the polymer).

In the bridge members of the formula I, $R^1$ and $R^2$ independently of one another preferably denote hydrogen or alkyl with 1 or 2 C atoms.

The bridge members of the formula I can all have exactly the same structure in the crosslinked copolymers according to the invention. This is the case if a single pure crosslinking substance of the formula Ia

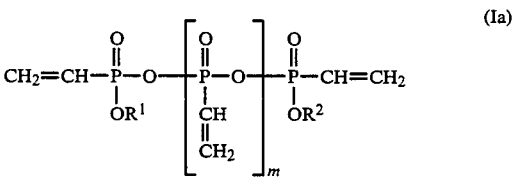

(Ia)

is used in the preparation of the products.

However, crosslinked copolymers according to the invention can also contain several types of structurally different bridge members. Thus, the bridge members can differ from one another in respect of the meaning of the radicals $R^1$ and $R^2$ and/or of the structural group index m, and in particular the structural group indices m can assume values from 0 to 6 in random distribution.

The frequency of the individual values for m can in each case be between 0 and 1, the frequency being defined as the proportion of a value m based on all the existing values for m. For example, if the bridge members in a product have m values between 0 and 6, and 35 out of each 100 bridge members have an m value of 1, 25 have an m value of 3, 20 have an m value of 4 and 5 have an m value of 6, the frequency for m=1 is 35/100=0.35; for m=3 is 25/100=0.25; for m=4 is 0.2 and for m=6 is 0.05.

The statement that the frequency of a specific m value in a product according to the invention is 1 means that this product contains exclusively bridge members with this specific m value; if the frequency of a specific m value in a copolymer according to the invention is 0, this means that no bridge members with this specific m value occur in this copolymer.

In practice, copolymers according to the invention which contain various crosslinking bridge members with different m values are particularly advantageous because, while having good technological properties, they can be prepared considerably more easily and hence with less expense. The crosslinking substances of the formula Ia used to introduce the bridge members into the macromolecules can be prepared as single substances only in a relatively involved manner. However, mixtures of these substances are easy to obtain, for example by a process described in European Patent Application Publication No. 32,663. In the European Patent Application mentioned, such mixtures have been defined by the formula

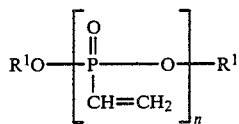

wherein $R^1$ denotes hydrogen or alkyl with 1–4 C atoms and n can in practice assume values from 1 to 8.

Such mixtures can be employed as such for the preparation of the products according to the invention without disadvantages. Preferred crosslinked copolymers according to the invention are then obtained, in which, in random distribution of the structural group indices m, the frequency of the individual m values correlates with the frequency of the values for n in a crude product from the preparation of compounds of the formula II

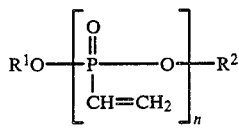

according to European Patent Application Publication No. 32,663, and in particular such that the frequency of a value m is equal to the frequency of that value n which satisfies the relationship $n = m + 2$.

The individual types of bridge members are as a rule randomly distributed in the macromolecules of the copolymers according to the invention.

Experience has shown that deviations from purely random distribution of the bridge members and also of the monomers in the basic chains after nothing in the technologcal usefulness of the crosslinked copolymers according to the invention. Slight deviations from purely random distribution can arise merely from the different reactivity of the monomers and crosslinking agents.

The crosslinked copolymers according to the invention contain 0.01 to 30% by weight, prefereably 0.01 to 6% by weight and in particular 0.05 to 2% by weight, of bridge members of the formula I and 99.99 to 70% by weight, preferably 99.99 to 94% by weight and in particular 99.95 to 98% by weight, of basic chain units. The vinyl groups which are present in the crosslinking agents of the formula Ia and are built into the basic chains during copolymerisation are also included in the % by weight proportion of the bridge members.

The basic chain units of the crosslinked copolymers according to the invention correspond to the formula III

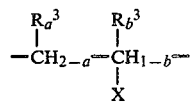

wherein $R^3$ is hydrogen or methyl, a and b each have the value 0 or 1 and the sum $a+b$ is likewise 0 or 1 and X is the carboximide group —$CONH_2$; a group of the formula IV

wherein $R^4$ and $R^5$ independently of one another represent hydrogen, methyl, or ethyl or together represent trimethylene or pentamethylene; carboxyl or a salt thereof with a cation $m^+$; alkoxycarbonyl with 1 to 6, preferably 1 to 3, carbon atoms or hydroxyalkoxycarbonyl with 1 to 3 carbon atoms; N-methylolcarboxamide of the formula $$HOCH_2NH—CO—$$

the methylol group of which can optionally be etherified with alkanols with 1 to 4 carbon atoms; alkanoylamino with 1 to 4 carbon atoms, which can optionally be N-substituted by methylol or alkyl with 1 to 4 carbon atoms; cyano; optionally substituted phenyl or benzyl; imidazol-1-yl; the sulphonic acid group; sulphoalkylamidocarbonyl with 1 to 4 carbon atoms in the alkyl radical; the phosponic acid group, it also being possible for the sulphonic acid and phosphonic acid groups to be in the form of their salts with a cation $M^+$; the phosphonic acid ester group of the formula V

wherein $R^6$ is alkyl with 1 to 4, preferably 1 or 2, C atoms; a radical of the formula VI

wherein $R^7$ and $R^8$ are identical or different and represent alkyl with 1 to 7, preferably 1 or 2, C atoms; a radical of the formula VII

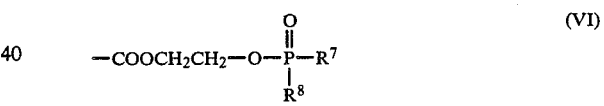

wherein $R^7$ and $R^8$ have the abovementioned meanings and p represents a number from 1 to 4; or a radical of the formula VIII

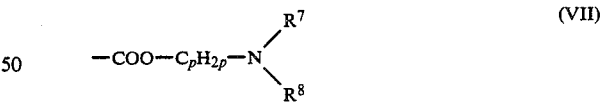

wherein $R^9$ and $R^{10}$ are identical or different and represent alkyl with 1 to 4, preferably 1 or 2, C atoms and p represents a number from 1 to 4; and the groups which correspond to the formulae VII and VIII and are quaternised, for example by dimethyl sulphate or methyl chloride.

A phenyl nucleus X and the phenyl nucleus of a benzyl nucleus are either unsubstituted or carry 1 or 2 substituents.

Suitable conventional substituents are halogen and alkyl with 1 to 4 C atoms, in particular chlorine, methyl and ethyl. Monosubstitution can be in the o-, m- or p-position relative to the vinyl or allyl group and disubstitution can preferably be in the 2,4- or 2,6-position, but also in the 2,5-, 3,5- or 3,4-position.

If X denotes phenyl or benzyl, the radicals which are only monosubstituted in the aromatic nucleus are preferred, and the unsubstituted radicals are particularly preferred.

Other substituents which a phenyl or benzyl radical X can carry are alkoxy with 1 or 2 C atoms, fluorine, trifluoromethyl or nitro.

In order to obtain the desired hydrophilic character of the copolymers according to the invention, care should be taken to ensure that at least 70% of the basic chain units contain such radicals X which have hydropilic character, and at least about 2%, preferably at least 7%, of the radicals X contain acid groups or salts thereof with the cation $M^+$.

Typical groups which have hydrophilic character are the sulphonic acid radical or carboxyl and groups X which carry these acid radicals, carboxamide ($-CONH_2$) and its methylol derivative, and the group of the formula IV.

Examples of typical groups without hydrophilic character are cyano, phenyl and benzyl.

The cation $M^+$ can in principle be derived from any known water-soluble base, the strength of which is sufficient to neutralise the sulphonic acid groups or carboxyl groups of the cross-linked copolymers according to the invention and which does not impair the hydrophilicity thereof. It can thus be selected in a simple known manner.

However, $M^+$ advantageously denotes an alkaline earth metal or, preferably, an alkali metal cation, in particular a sodium or potassium cation, or ammonium or a cation derived from lower aliphatic amines. Lower aliphatic amines from which the cations $M^+$ can be derived are primary, secondary or tertiary and have alkyl groups which have 1 to 4 C atoms and are optionally substituted by $-OH$ groups. Those which contain at least one β-hydroxyethyl radical are preferred, such as, for example, β-aminoethanol, β-dimethylaminoethanol, bis-(β-hydroxyethyl)-methylamine, tris-(β-hydroxyethyl)-amine, diethyl-β-hydroxyethylamine and bis-(β-hydroxyethyl)-ethylamine.

Preferred crosslinked copolymers according to the invention are those in which the basic chains are built up from units of the formula IX

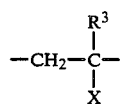

(IX)

wherein $R^3$ has the abovementioned meaning and X denotes the carboxamide group $-CONH_2$; a group of the formula IV

(IV)

wherein $R^4$ and $R^5$ independently of one another represent hydrogen, methyl or ethyl or together represent trimethylene or pentamethylene; carboxyl or alkali metal or ammonium salts thereof or hydroxyalkoxycarbonyl with 2 or 3, preferably 2, C atoms; the sulphonic acid groups; sulphoalkylamidocarbonyl with 1 to 4 C atoms in the alkyl radical, preferably a group of the formula

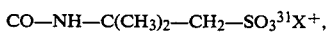

$CO-NH-C(CH_3)_2-CH_2-SO_3^{31}X^+$, the phosphonic acid group, it also being possible for the sulphonic acid and phosphonic acid groups to be in the form of their alkali metal or ammonium salts; or the phosphonic acid ester group of the formula V

(V)

wherein $R^6$ denotes alkyl with 1 to 4, preferably 1 or 2, C atoms.

Other preferred crosslinked copolymers according to the invention are those in which, based on the total amount by weight of the basic chains, X is a sulpho group or sulphoalkylamidocarbonyl group with 1 to 4 C atoms in the alkyl radical in 5 to 70% by weight, in particular in 10 to 65% by weight, of the basic chain units of the formula III, X is a group of the formula IV

(IV)

in 0 to 40% by weight, in particular in 0 to 25% by weight, of the basic chain units of the formula III, and X has one of the other abovementioned meanings in 30 to 95% by weight, in particular in 30 to 80% by weight, of the basic chain units of the formula III.

As a rule, the radicals X have not more than 10, preferably not more than 6, different meanings in an individual macromolecule.

Those crosslinked copolymers according to the invention in which several of the abovementioned preferred features are combined are particularly preferred.

The preparation of water-soluble polymers containing sulphonic acid groups built into the macromolecule has already been described in detail in numerous patents and in the specialist literature. Thus, for example, the synthesis of copolymers of vinylsulphonic acid with acrylamide and vinylpyrrolidone has been published in *J. Polymer Sci.*, 38, 147 (1959).

A process for the preparation of water-soluble copolymers of vinylsulphonic acid and acrylonitrile or methacrylonitrile, if appropriate mixed with other ethylenically unsaturatated compounds, has been described in German Pat. No. 1,101,760. Copolymers of vinyl- or alkyl-sulphonates with acrylamide and vinlyamides have been described, for example, in German Auslegeschrift No. 2,444,108.

Water-soluble copolymers which contain 2-acrylamido-2-methyl-propane-1-sulphonic acid, abbreviated to AIBA below, as a comonomer are described in U.S. Pat. Nos. 3,953,342, 3,768,565, 3,907,927 and 3,926,718 and in German Offenlegungschriften Nos. 2,502,012 and 2,547,773.

The crosslinked copolymers according to the invention containing radicals of the formula IV in which $R^3$ and $R^4$ together denote trimethylene or pentamethylene can be prepared in the manner known from the prior art, for example according to the statements in U.S. Pat. No. 3,929,741, by reaction of the monomers at temperatures of about 10 to 120° C., preferably at 40° to 80° C., in the presence of suitable polymerisation catalysts.

If the intention is to carry out, under analogous conditions, the copolymerisation of AIBA, styrene- or vinyl-sulphonic acid and non-cylic N-vinylamides of the formula Iva

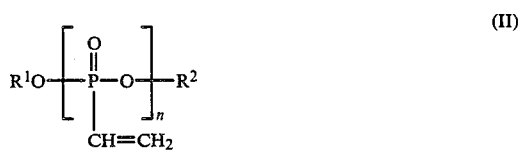

in order to prepare crosslinked copolymers according to the invention containing groups of the formula IV in which $R^4$ and $R^5$ do not together represent trimethylene or pentamethylene, it is necessary to convert the acid components into salts with the cation $M^+$ before the polymerisation by addition of bases. The bases advantageously used here are the hydroxides or salts of the cations $M^+$ with weak acids, such as, for example, carbonic acid or phosphoric acid, or, in the case of amine bases, $NH_3$ or the free amines, which have already been mentioned specifically above.

However, it is also possible, and as a rule even advantageous, in the copolymerisation of cyclic compounds Iva, to neutralise the acid components before the polymerisation.

Thus, for the preparation of each 100 parts by weight of the copolymer, it is advantageous to copolymerise 0.01 to 30 parts by weight, preferably 0.01 to 6 and in particular 0.05 to 2 parts by weight, of a crosslinking agent of the formula Ia

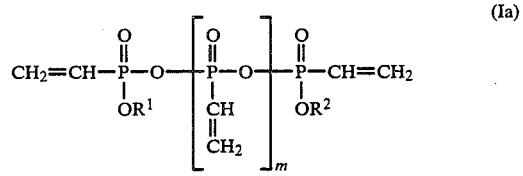

wherein $R^1$, $R^2$ and m have the abovementioned meanings, in the pure form or as a mixture of several compounds of this general formula, with 70 to 99.99 parts by weight, preferably with 94 to 99.99 and in particular 98 to 99.95 parts by weight, of comonomers of the formula IIIa

and, preferably, of those of the formula Ixa

wherein $R^3$, X, a and b have the abovementioned meanings and the abovementioned relationship exists between a and b, whereupon, if a comonomer of the formula IIIa is used in which X is a group of the formula IV wherein $R^4$ and $R^5$ do not together form a trimethylene or pentamethylene group the acid groups are necessarily neutralised and, if no such comonomer is used, the acid groups are neutralised, if appropriate, by addition of a base, the copolymerisation being initiated in a manner which is known per se and carried out at 10 to 120° C.

In the preparation of the crosslinked copolymers according to the invention, it is particularly advantageous not to use a pure compound of the formula Ia as the crosslinking agent but to use a crude product from the preparation of compounds of the formula II

according to European Patent Application Publication No. 32,663.

In this case, crosslinked copolymers according to the invention are obtained which contain several different bridge members of the formula I and, within the random distribution of the structural bridge indices m, the frequency of the individual m values correlates with the frequency of the values for n in the crude product used such that the frequency of a value m is equal to the frequency of that value n which satisfies the relationship $n = m + 2$.

Preferred copolymers according to the invention are also obtained if X is a sulpho group or sulphoalkylamidocarbonyl group with 1 to 4 C atoms in the alkyl radical in 5 to 70% by weight, in particular in 10 to 65% by weight, of the comonomers of the formula IIIa, X is a group of the formula IV in 0 to 40% by weight, in particular in 0 to 25% by weight, of the comonomers of the formula IIIa and X has one of the other abovementioned meanings in 30 to 95% by weight, in particular in 30 to 80% by weight, of the comonomers of the formula IIIa.

The polymerisation can be carried out as gel polymerisation, as precipitation polymerisation or in reverse emulsion.

If the copolymerisation is carried out in a water-miscible organic solvent, the conditions of precipitation polymerisation apply. The polymer is here obtained directly in solid form and can be isolated by distilling off the solvent or filtration with suction and drying.

Possible water-miscible organic solvents which are suitable for carrying out the preparation process according to the invention are, in particular, water-soluble alkanols, specifically those with 1 to 4 C atoms, such as methanol, ethanol, propanol, isopropanol, n-, sec.- or iso-butanol and, preferably, tert.-butanol.

The water content of the lower alkanols used here as the solvent should not exceed 6% by weight, since otherwise formation of lumps may occur during the polymerisation. The polymerisation is preferably carried out with a water content of 0–3% by weight.

The amount of solvent to be employed depends to a certain degree on the nature of the comonomers used.

As a rule, 200 to 1,000 g of the solvent are employed per 100 g of total monomers.

If the polymerisation is carried out in reverse emulsion, the aqueous monomer solution is emulsified in a known manner in a water-immiscible organic solvent, such as cyclohexane, toluene, xylene, heptane or high-boiling benzine fractions, with addition of 0.5–8% by weight, preferably 1–4% by weight, of known emulsifiers of the water-in-oil type, and the polymerisation is effected with the customary initiators which form free radicals.

The principle of inverse emulsion polymerisation is known from U.S. Pat. No. 3,284,393. In this process, water-soluble monomers or mixtures thereof are polymerised to high molecular weight copolymers under the influence of heat by first emulsifying the monomers, or aqueous solutions thereof, with addition of water-in-oil emulsifiers, in a water-immiscible organic solvent which forms the continuous phase, and warming this emulsion in the presence of free radical initiators. The comonomers to be used can be emulsified as such in the water-immiscible organic solvent, or they can be used in the form of an aqueous solution containing between 100 and 5% by weight of comonomers and 0 to 95% by weight of water, the composition of the aqueous solution depending on the solubility of the comonomers in water and the envisaged polymerisation temperature. The ratio between the water and the monomer phase can be varied within wide limits and is as a rule 70:30 to 30:70.

In order to emulsify the monomer phase in the water-immiscible organic solvent to give a water-in-oil emulsion, 0.1 to 10 percent by weight, based on the oil phase, of a water-in-oil emulsifier is added to the mixtures. Those emulsifiers which have a relatively low HLB value are preferably used. In principle, any inert water-insoluble liquid, that is to say in principle any hydrophobic organic solvent, can be used as the oil phase. In general, in the context of the present invention, hydrocarbons with a boiling point in the range from 120° to 350° C. are used. These hydrocarbons can be saturated, linear or branched paraffin hydrocarbons, such as predominantly exist in petroleum fractions, it being possible for these also to contain the usual contents of naphthene hydrocarbons. However, it is also possible to use aromatic hydrocarbons, such as, for example, toluene or xylene, and mixtures of the abovementioned hydrocarbons as the oil phase. A mixture of saturated normal- and iso-paraffin hydrocarbons containing up to 20 percent by weight of napthenes is preferably used.

A detailed description of the process can be found, for example, in German Patent Specification No. 1,089,173 and U.S. Pat. Nos. 3,284,393 and 3,624,019.

Crosslinked copolymers with a particularly high degree of polymerisation in the basic chains are obtained if the polymerisation is carried out in aqueous solution by the so-called gel polymerisation process. In this, 15 to 60% strength aqueous solutions of the comonomers are polymerised with known suitable catalyst systems without mechanical mixing, utilising the Trommsdorff-Norrisch effect (*Bios Final Rep.* 363,22; *Makromol. Chem.* 1, 169 (1947)).

The polymerisation reaction is carried out in the temperature range between −20° C. and 150° C., preferably between 5° and 90° C., it being possible to carry out the reaction either under normal pressure or under increased pressure. The polymerisation is as a rule carried out in an inert gas atmosphere, preferably under nitrogen.

The polymerisation can be initiated using high-energy electromagnetic rays or the usual chemical polymerisation initiators, for example organic peroxides, such as benzoyl peroxide, tert.-butyl hydroperoxide, methyl ethyl ketone peroxide or cumene hydroperoxide, azo compounds, such as azo-diisobutyronitrile or 2′-azo-bis-(2-amidinopropane) dihydrochloride

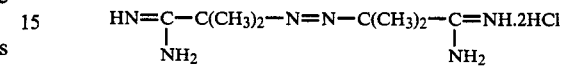

or inorganic peroxy compounds, such as $(NH_4)_2S_2O_8$, $K_2S_2O_8$ or $H_2O_2$, if appropriate in combination with reducing agents, such as sodium bisulphite and iron-II sulphate, or redox systems which contain, as the reducing component, an aliphatic or aromatic sulphinic acid, such as benzenesulphinic acid and toluenesulphinic acid or derivatives of these acids, such as, for example, Mannich adducts of sulphinic acid, aldehydes and amino compounds, such as are described in German Patent Specification No. 1,301,566. As a rule 0.03 to 2 g of the polymerisation initiator are used per 100 g of total monomers.

The addition to the polymerisation batches of small amounts of so-called moderators which harmonise the course of the reaction in that they flatten the rate of reaction/time diagram is also known. These moderators thus lead to an improvement in the reproducibility of the reaction and hence make it possible to prepare uniform products with exceptionally small deviations in quality. Examples of suitable moderators of this type are nitrilo-tris-propionylamide and monoalkylamines, dialkylamines or trialkylamines, such as, for example, dibutylamine. Such moderators can also advantageously be used in the preparation of the copolymers according to the invention.

So-called regulators can also be added to the polymerisation batches; these are compounds which influence the molecular weight of the polymers prepared. Examples of known regulators which can be used are alcohols, such as methanol, ethanol, propanol, isopropanol, n-butanol, sec.-butanol and the amyl alcohols, alkylmercaptans, such as, for example dodecylmercaptan and tert.-dodecylmercaptan, isooctylthioglycolate and some halogen compounds, such as, for example, carbon tetrachloride, chloroform and methylene chloride.

The quality properties of the polymers can be further improved by a procedure in which the polymer gels obtained by the gel polymerisation process are after-heated for several hours in the temperature range from 50° to 130° C., preferably from 70° to 100° C.

The crosslinked copolymers according to the invention which are prepared by this route and are in the form of aqueous gels can be dried, after mechanical comminution, and obtained in solid form.

As has already been mentioned above, the new polymers according to the invention are outstandingly suitable, for example, for the preparation of acid-soluble coating and encapsulation materials and as adsorbents for aqueous liquids. Moreover, they are excellently suited as auxiliaries for reducing the water loss in cement slurries, in particular for cementing deep drillings and tunnels, and as auxiliaries for the dyeing of textiles, in particular in pad-dyeing, where they caused a drastic increase in the liquor pickup and yield dyeings of high saturation and levelness.

The following embodiment examples illustrate the preparation and use of the crosslinked copolymers according to the invention.

Where the crosslinking agent of the formula I has been used in the examples in the form of a crude product of the process according to European Patent Application Publication No. 32,663, it has been called "vinylphosphonic acid anhydride" (VPAA).

The following abbreviations for the monomers employed in the examples and tabular examples have otherwise been utilized:
AM = acrylamide
AIBA = 2-acrylamido-2-methyl-propane-1-sulphonic acid
VPA = vinylphosphonic acid
VPE = vinylphosphonic acid ethyl ester
VIMA = vinyl-methyl-acetamide
VIFA = vinylformamide
AA = acrylic acid
VIPY = vinylpyrrolidone
MAA = methacrylic acid
VSAna = vinylsulphonic acid sodium salt
StyreneSA = styrenesulphonic acid

EXAMPLE 1

Emulsion polymerisation 7.2 g of $^R$ Arkopal N 100 (non-ionic emulsifier based on an oxyethylated phenol derivative) and 19.4 g of $^R$ Span 80 (non-ionic emulsifier based on a sugar-alcohol stearate) are dissolved in $^R$ Isopar M (technical mixture of isoparaffin with a boiling point of about 200°–240° C.) and the resulting solution is poured into a 1 liter reaction vessel equipped with a stirrer, thermometer and a nitrogen inlet. A monomer solution is then prepared by dissolving 97.2 g of acrylamide, 9.7 g of AIBA, 2.0 g of vinylphosphonic acid (VPA) and 0.5 g of a compound of the general formula Ia wherein m=0 and $R^1$ and $R^2$ are hydrogen, in 105 ml of water. The pH value of the monomer solution is brought to 8.5 with ammonia (25% strength). The aqueous monomer solution is added to the organic phase, with rapid stirring. The reaction vessel is evacuated and then filled with nitrogen. A solution of 0.0275 g of ammonium persulphate in 3 ml of water is now added to the mixture and the polymerisation is thus started. The reaction lasts 1.5 hours and the reaction temperature is kept between 30° and 40° C. A stable emulsion results, which can be inverted in water in a manner which is known per se, using commercially available surface-active agents, a highly viscous thixotropic polymer formulation being formed.

EXAMPLE 2

Gel polymerisation

A monomer solution is prepared in a polymerisation flask of 1 liter capacity and equipped with a ground-glass lid, stirrer, thermometer and gas inlet tube, by dissolving 60 g of acrylamide, 30 g of AIBA and 10 g of crude vinylphosphonic acid methyl ester, prepared by the process of European Patent Application Publication No. 32,663 and containing 0.5 g of compounds of the formula

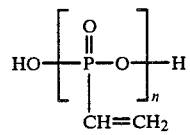

in which n is 2 or >2, in 250 g of water. The pH value is brought to 8.5 with ammonia (25% strength). 1 g of an aqueous 10% strength dibutylamine HCl solution and 0.1 g of ammonium persulphate are now added, while stirring and passing in nitrogen. The mixture is stirred at an increased speed for a further 3 minutes, while passing in nitrogen. The passing in of nitrogen is stopped and the inlet tube and stirrer are raised. After an induction time of 30 minutes, the polymerisation starts, whereupon the temperature rises from 20° C. to 78° C. and the solution is transformed into a dimensionally stable gel. This or a powder prepared therefrom by drying and grinding is swellable in water and soluble 2–25% strength aqueous HCl. K value: 197.8

EXAMPLE 3

Precipitation polymerisation 49.7 g of acrylamide, 7.1 g of AIBA, 10.7 g of VPE, 3.6 g of methacrylic acid (MAA) and 1 g of vinylphosphonic acid anhydride are dissolved in 440 ml of tert.-butanol in a polymerisation flask of 1 liter capacity and equipped with a stirrer, reflux condenser, thermometer, dropping funnel and gas inlet tube. The monomer solution is heated to 50° C., while stirring and passing in nitrogen, and 1 g of azoisobutyronitrile, dissolved in 5 ml of dimethylformamide, is added dropwise. After an induction time of 30 minutes, the polymerisation starts, the reaction temperature increases to 68° C. and the polymer preciptates. It is after-heated at 80° C. for a further 2 hours. The copolymer can be isolated by filtration with suction and drying. However, the solvent can also be distilled off directly under reduced pressure. The polymer is obtained in the form of a white light powder, which is swellable in water but dissolves in 10% strength aqueous HCl, and has a K value of 108.1.

The vinylphosphonic acid anhydride used above is obtained in a known manner by hydrolysis of 2 mol of vinyl-phosphonic acid dichloride with 3 mol of water.

A product which is likewise swellable in water but dissolves significantly more slowly in 10% strength aqueous HCL is obtained if 44.0 g of acrylamide, 7.0 g of AIBA, 10 g of VPE, 4 g of methacrylic acid and 4 g of vinylphosphonic acid anhydride are used analogously.

EXAMPLE 4

Gel polymerisation

A monomer solution is prepared in a polymerisation flask of 1 liter capacity and equipped with a ground-glass lid, stirrer, thermometer and gas inlet tube, by dissolving 65 g of acrylamide, 4.5 g of AIBA and 0.5 g of a vinylphosphonic acid methyl ester-anhydride of the formula Ib

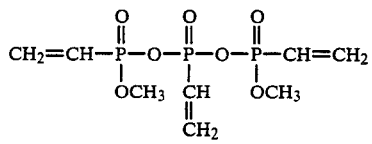

in 250 g of water. The pH value is brought to 8.5 with ammonia (25% strength). 1 g of an aqueous 10% strength dibutylamine HCL solution and 0.1 g of ammonium persulphate are now added, while stirring and passing in nitrogen. The mixture is stirred at an increased speed for a further 3 minutes, while passing in nitrogen. The passing in of nitrogen is stopped and the inlet tube and stirrer are raised. After an induction time of 30 minutes, the polymerisation starts, whereupon the temperature rises from 20° C. to 78° C. and a dimensionally stable gel is formed.

A product which swells greatly in water and is soluble in 2% strength hydrochloric acid can be obtained by drying the comminuted gel.

The vinylphosphonic acid methyl ester-anhydride used as the crosslinking agent above was prepared by reacting 2 mol of vinylphosphonic acid monomethyl ester with 1 mol of vinylphosphonic acid dichloride at 80° C. in a manner which is known per se.

A product with virtually the same properties is obtained if, instead of the crosslinking agent of the formula Ib used above, the corresponding dibutyl ester of the formula Ic

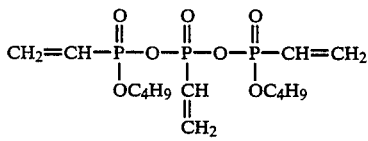

which can be prepared analogously, is employed.

EXAMPLE 5

Precipitation polymerisation 49.7 g of acrylamide, 7.1 g of AIBA, 10.7 g of VPE, 3.6 g of methacrylic acid (MAA) and 1 g of a vinylphosphonic acid anhydride of the formula Id

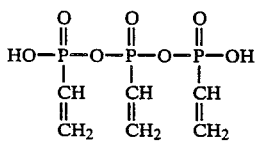

(corresponding to a compound of the formula Ia where $m=1$ and $R^1=R^2=$hydrogen) are dissolved in 440 ml of tert.-butanol in a polymerisation flask of 1 liter capacity and equipped with a stirrer, reflux condenser, thermometer, dropping funnel and gas inlet tube. The monomer solution is heated to 50° C., while stirring and passing in nitrogen, and 1 g of azoisobutyronitrile, dissolved in 5 ml of dimethylformamide, is added dropwise. After an induction time of 30 minutes, the polymerisation starts, the reaction temperature rises to 68° C. and the polymer precipitates. The mixture is after-heated at 80° C. for a further 2 hours. The copolymer can be isolated by filtration with suction and drying. However, the solvent can also be distilled off directly under reduced pressure. The polymer is obtained in the form of a white light powder which is swellable in water but dissolves in 10% strength aqueous HCl, and has a K value of 98.0.

EXAMPLE 6

Gel polymerisation

A monomer solution is prepared in a polymerisation flask of 1 liter capacity and equipped with a ground-glass lid, stirrer, thermometer and gas inlet tube, by dissolving 65 g of acrylamide, 4.5 g of AIBA and 1.5 g of a vinylphosphonic acid anhydride of the formula Ie

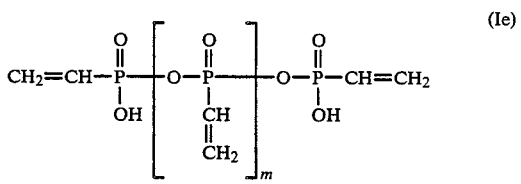

wherein m has a statistical average of 4.5, in 250 g of water. The pH value is brought to 8.5 with ammonia (25% strength). 1 g of an aqueous 10% strength dibutylamine HCl solution and 0.1 g of ammonium persulphate are now added, while stirring and passing in nitrogen. The mixture is stirred at an increased speed for a further 3 minutes, while passing in nitrogen. The passing in of nitrogen is stopped and the inlet tube and stirrer are raised. After an induction time of 30 minutes, the polymerisation starts, whereupon the temperature rises from 20° C. to 78° C. and a dimensionally stable gel is formed.

A product which swells greatly in water and is soluble in 2% strength hydrochloric acid is obtained by drying the comminuted gel.

The vinylphosphonic acid anhydride used above as the crosslinking agent is prepared by reacting 6 mol of vinylphosphonic acid dichcloride with 7 mol of water in a manner which is known per se.

EXAMPLE 7

Precipitation polymerisation 49.7 g of acrylamide, 7.1 g of AIBA, 10.7 g of VPE, 3.6 g of methacrylic acid (MAA), 0.4 g of a vinylphosphonic acid anhydride of the formula Id

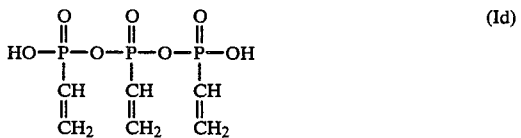

0.4 g of a vinylphosphonic acid ester-anhydride of the above formula Ib and 0.2 g of a vinylphosphonic acid ester-anhydride of the above formula Ic are dissolved in 440 mol of tert.-butanol in a polymerisation flask of 1 liter capacity and equipped with a stirrer, reflux condenser, thermometer, dropping funnel and gas inlet tube. The monomer solution is heated to 50° C., while stirring and passing in nitrogen, and 1 g of azoisobutyronitrile, dissolved in 5 ml of dimethylformamide, is added dropwise. After an induction time of 30 minutes, the polymerisation starts, the reaction temperature increases to 68° C. and the polymer precipitates. It is after-heated at 80° C. for a further 2 hours. The copolymer can be isolated by filtration with suction and drying. However, the solvent can also be distilled off directly under reduced pressure. The polymer is obtained in the form of a white light powder, which is swellable in water but dissolves in 10% strength aqueous HCl, and has a K value of 110.

The copolymers of the following table can also be prepared according to these procedures.

For carrying out the test, 500 g of class G cement and 250 g of saturated sodium chloride solution are made into a homogeneous paste and 2.5 g of a copolymer of the invention listed in the following table are added with uniform stirring. Thereafter, the filtration test according to APJ Code 29 is immediately carried out. Control study, cement paste without addition of the

|     | VPA$^A$ | AM   | AI$^{BA}$ | VP$^A$ | VPE  | VIMA | VIFA | AA  | VIPY | MA$^A$ | VSANa | Styrene SA | Viscosity [cp] |
|-----|---------|------|-----------|--------|------|------|------|-----|------|--------|-------|------------|----------------|
| 1   | 0.2     | 50   | 20        | 4.8    | 5.0  | 10   |      | 5   |      | 5      |       |            | 48             |
| 2   | 1.0     | 40   | 9         |        | 5.0  | 10   | 10   |     | 15   | 10     |       |            |                |
| 3   | 0.5     | 45   | 15        | 24.5   |      | 10   |      | 5   |      |        |       |            |                |
| 4   | 1.0     | 25   | 10        | 30     | 9    |      | 5    | 20  |      |        |       |            |                |
| 5   | 0.3     | 5    | 20        | 74.7   |      |      |      |     |      |        | 8     |            |                |
| 6   | 2.0     | 50   | 9         | 31     |      |      |      |     |      |        |       |            | 29             |
| 7   | 0.1     | 40   | 9         | 20.9   | 10   |      | 10   |     | 5    |        |       | 5          |                |
| 8   | 0.2     | 50   | 10        | 10     | 24.8 |      |      | 15  | 10   |        |       |            |                |
| 9   | 0.3     | 50   | 10        | 10     | 24.8 |      |      |     | 10   | 15     |       |            |                |
| 10  | 0.5     | 30   | 20        | 20     | 2.5  | 7    | 10   |     |      | 10     |       |            | 17             |
| 11  | 2.0     | 25   | 15        | 8      |      | 30   |      | 20  |      |        |       |            |                |
| 12  | 2.0     | 30   | 20        | 25     | 3.0  |      | 12   |     |      |        |       | 10         |                |
| 13  | 1.0     | 10   | 9         | 10     |      | 70   |      |     |      |        |       |            |                |
| 14  | 3.0     | 5    | 80        | 2      |      |      |      | 10  |      |        |       |            |                |
| 15  | 0.5     | 90   | 5         | 2.5    | 2.0  |      |      |     |      |        |       |            |                |
| 16  | 0.2     | 95   | 2         | 2.8    |      |      |      |     |      |        |       |            | 53             |
| 17  | 0.1     | 98   | 1         | 0.9    |      |      |      |     |      |        |       |            | 84             |
| 18  | 0.3     | 85   | 5         | 1.7    | 3.0  |      | 5    |     |      |        |       |            | 107            |
| 19  | 0.5     | 90   | 7.5       | 1.0    |      |      |      |     |      |        | 1.0   |            |                |
| 20  | 0.5     | 50   | 30        | 5      | 5    |      | 4.5  | 5   |      |        |       |            |                |
| 21  | 0.1     | 60.9 | 20        | 9      | 2    |      |      |     | 8    |        |       |            |                |
| 22. | 0.3     | 40   | 15        | 5      | 4.7  | 15   |      |     | 10   | 10     |       |            |                |
| 23. | 0.3     | 80   | 10        | 4.7    | 5.0  |      |      |     |      |        |       |            | 48             |
| 24. | 1.0     | 70   | 20        | 5.0    | 4.0  |      |      |     |      |        |       |            | 205            |
| 25. | 2.0     | 70   | 20        | 5.0    | 3.0  |      |      |     |      |        |       |            |                |
| 26. | 5.0     | 70   | 20        | 5.0    |      |      |      |     |      |        |       |            |                |
| 27. | 10      | 70   | 20        |        |      |      |      |     |      |        |       |            | 108            |
| 28. | 15      | 70   | 10        | 2.0    | 3.0  |      |      |     |      |        |       |            |                |
| 29. | 20      | 70   | 10        |        |      |      |      |     |      |        |       |            |                |
| 30. | 30      | 60   | 5         | 20     | 3.0  |      |      |     |      |        |       |            | 13.2           |
| 31. | 0.4     | 60   | 35        | 2.6    | 2.0  |      |      |     |      |        |       |            |                |
| 32. | 0.2     | 60   | 36        | 2.8    | 1.0  |      |      |     |      |        |       |            |                |
| 33. | 0.1     | 60   | 36        | 2.9    | 1.0  |      |      |     |      |        |       |            |                |
| 34. | 0.5     | 30   | 60        | 2.5    | 1.0  |      | 6.0  |     |      |        |       |            | 318            |
| 35. | 0.1     | 30   | 60        | 2.9    | 1.0  | 6.0  |      |     |      |        |       |            |                |
| 36. | 0.5     | 30   | 50        | 2.5    | 1.0  | 10   |      | 6   |      |        |       |            |                |
| 37. | 1.5     | 50   | 20        | 2.5    | 1.0  |      |      |     | 20   |        | 5     | 5          |                |
| 38. | 2.5     | 60   | 10        | 2.5    |      | 10   |      |     |      | 10     |       | 5          |                |

APPLICATION EXAMPLE 1

Water Loss from Cement Slurry

A cement slurry which is employed for cementing rock cavities, such as wells for oil recovery or tunnels is in direct contact with partially porous rock formations, a fact which in normal cement mixtures results in too strong a water loss and thus in incomplete and non-uniform setting.

In order to achieve a technically unobjectionable cementing of wells and tunnel walls an attempt must be made to keep the water loss of the cement slurry used as low as possible. The water loss can be measured in the laboratory using a filter press and APJ Code 29, the filter area being 45.8±0.7 cm² and the excess pressure being 7±0.7 bar. The amount of water leaked from the cement slurry is measured after 30 minutes of filtering. The electrolyte stability of the retarding effect of the polymer addition is also of particular importance as operations in geological formations frequently take place in the presence of water-soluble salts and the water loss must be kept at a minimum under such conditions as well. In the laboratory test, therefore, a saturated NaCl solution is utilized as mixing water for the cement.

invention: water loss = 86 ml.

| Polymer Example No. | Water Loss APJ Code 29 (ml) |
|---------------------|------------------------------|
| 14                  | 12.3                         |
| 15                  | 15                           |
| 36                  | 16.8                         |

APPLICATION EXAMPLE 2

Pad-Dyeing Process

In pad-dyeing it is important to achieve a high and uniform liquor pickup. A cotton knitted fabric is padded at room temperature on a padding machine for knitted fabrics using a liquor which, per liter, contains 55 g of the reactive dye Reactive Black 5 (C.I. No. 20505), 8 g of a commercial wetting agent and 30 g of a 5% by weight thixotropic aqueous paste of a copolymer of Example 17. The fixing alkali required is metered into the color box trough. The liquor pickup is 145%. After an overnight standing time of the padded goods with slow rotation and the customary aftertreatment the cotton knitted fabric displays an unusually deep and excellently even dyeing.

Without polymer addition the liquor pickup is 103% at the same squeezing pressure. If the copolymer of Example 17 of the invention, employed above, is replaced by the same amount of the copolymers of Example 19 or 21 liquor pickups of respectively 161 and 138% at the same squeezing pressure are obtained.

APPLICATION EXAMPLE 3

Absorption of aqueous Liquids

For testing the absorptive capacity for aqueous liquids 1 g of pulverulent polymer is stirred into 500 ml of water. After 15 minutes the mixture is filtered off via a filter cloth and, as soon as no more water drips off, the weight of the remaining swollen gel particles is determined.

The following results were obtained using the copolymers of the invention listed in the table:

| Copolymer of Example no. | Weight of swollen Particles (g) |
|---|---|
| 15 | 65 |
| 23 | 85 |
| 24 | 60 |
| 25 | 51 |
| 26 | 34 |
| 30 | 22 |

What is claimed is:

1. In a crosslinked copolymer of olefinically unsaturated monomers crosslinked with a plurality of crosslinking members, the improvement comprises said crosslinking members being bridge members of the formula

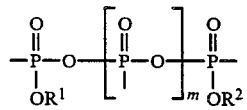

wherein $R^1$ and $R^2$ independently of one another are hydrogen or alkyl with 1 to 4 carbon atoms and m is a number from 0 to 6.

2. The crosslinked copolymer according to claim 1 wherein $R^1$ and $R^2$ independently of one another are hydrogen, methyl or ethyl.

3. The crosslinked copolymer according to claim 1 wherein m has values from 0 to 6 in random distribution.

4. The crosslinked copolymer according to claim 1 wherein the copolymer contains 0.01 to 30% by weight of said crosslinking bridge members.

5. The crosslinked copolymer according to claim 1 wherein the polymeric units being crosslinked comprise chain units containing moieties of the formulae:

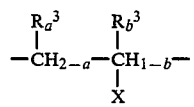

wherein $R^3$ is hydrogen or methyl, a and b are each 0 or 1 and the sum a+b is 0 or 1 and X is the carboxamide group —CONH$_2$;

wherein $R^4$ and $R^5$ independently of one another are hydrogen, methyl or ethyl or together are trimethylene or pentamethylene;
carboxyl or a salt thereof;
alkoxycarbonyl with 1 to 6 carbon atoms;
hydroxyalkoxycarbonyl with 1 to 3 carbon atoms;
N-methylolcarboxamide of the formula

wherein the methylol moiety is unetherified or etherified with alkanol having 1 to 4 carbon atoms;
alkanoylamino with 1 to 4 carbon atoms, unsubstituted or N-substituted by methylol or alkyl with 1 to 4 carbon atoms;
cyano;
phenyl or benzyl;
imidazol-1-yl; the sulphonic acid moiety or a salt thereof; sulphoalkylamidocarbonyl with 1 to 4 carbon atoms in the alkyl moiety or a salt thereof; the phosphonic acid moiety or a salt thereof;
the phosphonic acid ester of the formula

wherein $M^{\oplus}$ is a cation and $R^6$ is alkyl with 1 to 4 carbon atoms
a moiety of the formula

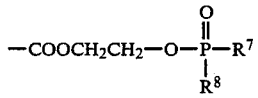

wherein $R^7$ and $R^8$ are identical or different and each is alkyl with 1 to 7 carbon atoms;
an amino moiety of the formula

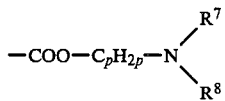

or its quaternary salt wherein p is a number from 1 to 4; or
an amino moiety of the formula

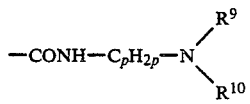

or its quaternary salt wherein $R^9$ and $R^{10}$ are identical or different and each is alkyl with 1 to 4 carbon atoms and p is a number from 1 to 4.

6. The crosslinked copolymer according to claim 1 wherein the polymeric units being crosslinked comprise chain units of the formula

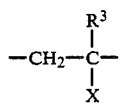

wherein R³ is hydrogen or methyl and X is —CONH₂; a moiety of the formula

wherein R⁴ and R⁵ independently of one another are each hydrogen, methyl or ethyl or together are trimethylene or pentamethylene;
carboxyl or the alkali metal or ammonium salts thereof;
hydroxyalkoxycarbonyl with 2 or 3 carbon atoms;
sulphonic acid moiety or a salt thereof;
sulphoalkylamidocarbonyl with 1 to 4 carbon atoms in the alkyl;
the phosphonic acid moiety or a salt thereof; or
the phosphonic acid ester of the formula

wherein R⁶ is alkyl with 1 to 4 carbon atoms.

7. The crosslinked copolymer according to claim 6 wherein X is a sulpho or sulphoalkylamidocarbonyl moiety with 1 to 4 alkyl carbon atoms in an amount of 5 to 70% by weight of the polymeric units being crosslinked or X is a moiety of the formula

in an amount of up to 40% by weight of the polymeric units being crosslinked.

* * * * *